(12) United States Patent
Grynkiewicz et al.

(10) Patent No.: US 8,178,609 B2
(45) Date of Patent: May 15, 2012

(54) ISOFLAVONES FOR TREATING MUCOPOLYSACCHARIDOSES

(75) Inventors: Grzegorz Grynkiewicz, Lomianki (PL); Grzegorz Wegrzyn, Gdańsk (PL); Barbara Szechner, Warszawa (PL); Wieslaw Szeja, Zernica (PL); Anna Tylki-Szymańska, Warszawa (PL); Alicja Wegrzyn, Gdańsk (PL); Joanna Jakobkiewicz-Banecka, Gdańsk (PL); Sylwia Barańska, Gdańsk (PL); Barbara Czartoryska, Warszawa (PL); Ewa Piotrowska, Olsztyn (PL)

(73) Assignee: Instytut Farmaceutyczny, Warszawa (PL)

( * ) Notice: Subject to any disclaimer, the term of this patent is extended or adjusted under 35 U.S.C. 154(b) by 823 days.

(21) Appl. No.: 12/067,289

(22) PCT Filed: Sep. 21, 2006

(86) PCT No.: PCT/PL2006/000064
§ 371 (c)(1),
(2), (4) Date: Nov. 5, 2008

(87) PCT Pub. No.: WO2007/035121
PCT Pub. Date: Mar. 29, 2007

(65) Prior Publication Data
US 2009/0062380 A1    Mar. 5, 2009

(30) Foreign Application Priority Data

Sep. 21, 2005    (PL) .......................................... 377180

(51) Int. Cl.
*A61K 47/32*    (2006.01)
(52) U.S. Cl. ........................................ 524/456; 549/403
(58) Field of Classification Search .................. 514/456; 549/403
See application file for complete search history.

(56) References Cited

U.S. PATENT DOCUMENTS
6,399,107 B1 *    6/2002    Kessler et al. ................ 424/646
* cited by examiner

*Primary Examiner* — Elli Peselev
(74) *Attorney, Agent, or Firm* — Matthias Scholl, PC; Matthias Scholl

(57) ABSTRACT

A method of treatment of mucopolysaccharidosis, the method including administering to a patient in the need of such treatment a therapeutically effective amount of a natural isoflavone of formula (I), a derivative thereof, or a pharmaceutically acceptable salt thereof. A pharmaceutical composition including a pharmaceutically acceptable excipient; and a natural isoflavone of formula (I), a derivative thereof, or a pharmaceutically acceptable salt thereof, the natural isoflavone, the derivative thereof, or the pharmaceutically acceptable salt threof being in a therapeutically effective amount for the treatment of mucopolysaccharidosis.

11 Claims, 2 Drawing Sheets

ISOFLAVONES FOR TREATING MUCOPOLYSACCHARIDOSES

FIELD OF THE INVENTION

The invention relates to the medical use of natural isoflavones and their semisynthetic derivatives for the therapeutic and/or prophylactic treatment of diseases, at the base of which lies an excessive production or storage of glycosaminoglycans, especially for treatment of mucopolysaccharidoses.

BACKGROUND OF THE INVENTION

The natural isoflavones, present in most of all vascular plants, constitute a subclass of flavonoids, characterized by presence of two benzene rings linked to a group of three carbon atoms in their linear or ring form.

The main flavone ingredients of seeds *Glycine max Merill* (soya-bean) constitute β-D-glycosides such as genistin, daidzin and glycitin, while the corresponding to them aglycones (genistein, daidzein and glycitein) occur in up to one hundred times smaller quantities and appear in more considerable amounts only when being technologically processed, under heat treatment or due to fermentation.

Genistein (4',5,7-trihydroxy-3-phenylchromen-4-on) is a competitive inhibitor for protein tyrosine kinases (PTK), playing important role as a structural analogue of adenosine triphosphate (ATP) (T. J. O'Dell et al., *Nature*, 353, p.558 (1991). Researches concerning the biological role of the enzymes from the PTK group in the transmission of chemical signals cascade from the cell membrane receptors to the nuclear effectors modulating the gene expression and transcription, constitute at present one of the most promising trends in the medical chemistry (P. W. Groundwater et al., *Progr. Med. Chem.*, 33, p. 233 (1996), at the same time it is expected that the selective phosphorylation inhibitors will give rise not only to a new generation of drugs, for instance antineoplastic drugs, but also to such compounds, which will enable to inhibit the oncogenesis, thus preventing neoplastic diseases.

In medical respect, the genistein is at present classified as phytoestrogen and included among the new class of biological active compounds termed selective estrogen receptors modulators (SERM).

In the Polish patent application nr 346955 and in the publication of K. Polkowski et al. (Cancer Letters 203(2004), 59-69) has been proved the cytotoxic and cytostatic activity in vitro of several ethereal and ester derivatives of genistein, in which one hydrogen atom of at least one hydroxyl group at the positions 7 and/or 4' has been replaced by fatty acid radical, alkyloaryl or saccharide groups. In this application like as in the Polish patent application nr 354794 have been also shown the manners for functionalizing the hydroxyl groups of genistein and a synthetic methodology applied to obtain new derivatives.

At the base of present invention lies the finding that genistein, like other isoflavones and semisynthetic derivatives thereof, causes a significant inhibition of glycosaminoglycans synthesis and in consequence of it would be useful for treatment of diseases caused by excessive production or storage of mucopolysaccharides.

The mucopolysaccharidoses (MPS) are the rare genetic conditions which inheritance is autosomal recessive (with exception of a mucopolysaccharidose of type II, MPS II, the inheritance of which is X-linked) (Kaye, *Curr. Treat Opinions Neurol.* 3 (2000), 249). The cause of each of the type of mucopolysaccharidose is a damage of a specific lysosomal enzyme taking part in the degradation of the mucopolysaccharides.

The mucopolysaccharides, at present called glycosaminoglycans (GAG), are chemical compounds produced by the most of tissues in mammals. They are among others responsible for the correct structure and functioning of connective tissue, for proper communication between the cells (including intracellular signaling owing to aided binding of signaling proteins with their receptors in the cell membranes) and for possibility of proper penetration of different substances into body tissues. Most of the glycosaminoglycans occur in form of peptidoglycans, that is to say are connected by a covalent bond (usually by a residue of serine) with a proper peptide. In the regular cell occurs the permanent turnover of the glycosaminoglycans, it means synthesis of the new and degradation of the elder molecules. The breakdown of these compounds in the cells take place in the lysosomes by participation of a dozen or so enzymes specifically directed to these organelles (Kaplan et al., *Proc. Natl. Acad. Sci. USA* 74(1977), 2026).

In case that one of the enzymes responsible for the breakdown of the mucopolysaccharides is deficient or its activity significantly decreased, they will not be degraded and accumulate in the lysosomes and in the intercellular space. The insufficiency of the lysosomal apparatus stimulates many compensatory processes, after depletion of which the complicated function and structure of the cell will be disturbed, leading to its destruction and in consequence of it gives rise to characteristic clinic symptoms. In the pathomechanism of these diseases the key significance has not only the mechanic results of the storage, but also the toxic and damaging effect of the accumulated compounds and cytokines.

Different types of mucopolysaccharidose disorders classified as Type I through IX and the deficient enzymes are listed in Table 1.

TABLE 1

Mucopolysaccharidoses classification*

| Type | Name of syndrome | Enzyme deficient |
|---|---|---|
| MPS I-H | Hurler syndrome | α-L-iduronidase |
| MPS I-S | Scheie syndrome | α-L-iduronidase |
| MPS I-H/S | Hurler-Scheie syndrome | α-L-iduronidase |
| MPS II | Hunter syndrome | iduronate sulphatase |
| MPS III A | Sanfilippo syndrome type A | heparan-N-sulphatase |
| MPS III B | Sanfilippo syndrome type B | N-acetyl-α-D-glucosaminidase |
| MPS III C | Sanfilippo syndrome type C | CoA-α-glucosaminide-N-acetyltransferase |
| MPS III D | Sanfilippo syndrome type D | N-acetyl-α-D-glucosaminide-6-sulfatase |
| MPS IV A | Morquio syndrome type A | N-acetyl-α-D-glucosaminide-6-sulfatase |
| MPS IV B | Morquio syndrome type B | B-galactosidase |
| MPS VI | Maroteaux-Lamy syndrome | N-acetylgalactosamine-4-sulfatase (acetylsulfatase) |
| MPS VII | Sly syndrome | B-glucuronidase |
| MPS IX | — | hyaluronidase |

*Neufeld, E. F. and Muenzer, J., *The mucopolysaccharidoses*. In: Scriver, C. R., Beaudet, A. L., Sly, W. S., Valle, D. (ed.): *The metabolic and molecular bases of inherited diseases*. New York: McGraw-Hill Co, 2001, 3421-3452;
Wegrzyn G., Mukopolisacharydozy. *Praktyka i Klinika Medyczna*, 4/5 (2000), 5-18.

The accumulation of mucopolysaccharides in the lyzosomes causes the gradually function impairment of cells, tissues and practically all the organs. These diseases have a progressing character and a middle time of patient's survival amounts a dozen or so years.

Up to the present time in case of all mucopolysaccharidoses only symptomatic treatment was possible, not very efficient, although it could to a certain degree improve the comfort of life of the sick people. Some hopes were set on bone marrow transplantation, in order to introduce the cells producing the lacking enzymes to the organism of the sick person (Schiffmann and Brady, *Drugs*, 62(2002), 733). This method proved not to be very efficient and at the same time it is connected with a higher risk of complications. Since recently replacement therapy of mucopolysaccharidose of type I became possible, based on intravenous administration of the lacking recombinant enzyme—the α-L-iduronidase (Kakkis, *Expert Opin. Investig. Drugs*, 11(2002), 675). Although clinical research has shown a very high efficacy of this type of treatment towards most of the organs, it must be say that because of the blood-brain barrier as a serious problem remain disturbances in functioning of the central nervous system, found in part of patients with MPS 1 (especially in type MPS 1-H).

Enzymatic replacement therapy in case of MPS 1 is actually the only one accessible method of causal treatment of mucopolysaccharidoses. Other MPS types are not treated at all or only symptomatic treatment could be applied, which proved to be not very effective. Consequently there is an urgent necessity to look for therapeutic methods for this group of chronic diseases, which in the absence of treatment lead to the premature death of patients.

The greatest problem by introducing enzymatic replacement therapy in other MPS types is the fact that in many types of this disease (MPS II, MPS IIIA, MPS IIIB, MPS IIIC, MPS IIID, MPS VII) severe neurological symptoms may occur related to the central nervous system, while in others types the largest changes are observed in the osteoarticular system (MPS IVA, MPS IVB, MPS VI). The penetration of the intravenously administered enzyme into the central nervous system is minimal, whereas into the bone is very impeded.

An approach to the treatment of mucopolysaccharidoses being alternative to the enzymatic replacement therapy can constitute the inhibition of the synthesis of the substrate, which can not be degraded in the organisms of sick individuals (Wegrzyn et al., *Med. Hypothes.*, 62 (2004), 986).

The present invention is based on an unexpected finding that the natural isoflavone, genistein, added to the cultured fibroblasts derived from patients affected with MPS, in the concentration range of 10-30 micromoles/l, causes significant inhibition of glycosaminoglycans synthesis. The incubations of cells derived from patients affected with different MPS types (MPS I, MPS II, MPS IIIA and MPS IIIB) with genistein has proved that in these cells the level of glycosaminoglycans not only did not increase but on the contrary significantly decreased, reaching after six days a level almost identical with the normal one. The results of these tests have been confirmed by electron microscope investigations of the cells, where the disappearance of deposits in fibroblasts cultured during one week in presence of genistein (in concentration of 10 micromolar units) has been observed. Similar effects were observed in consequence of fibroblasts incubation in presence of a soya-bean isoflavones extract, what indicates that these compounds and their derivatives could have similar activity as in the case of genistein.

The molecular mechanism of genistein activity as inhibitor of glycosaminoglycans synthesis has not been recognized, although it seems to be likely that it is related to the previous founding to inhibit tyrosine kinase activity of the epidermal growth factor receptor (EGFr) (Akiyama et al., *J. Biol. Chem.*, 262(1987), 5592). This factor is in turn essential for the effective glycosaminoglycans synthesis (Tirone et al., *J. Biol. Chem.*, 272(1997), 4787). Activation of EFGr can probably stimulate the system of intracellular signal transmission, leading to the effective expression of genes, which are coding the enzymes related to the process of glycosaminoglycans synthesis. The fact, already proved, that the intravenously administered genistein crosses the blood-brain barrier in a rat with an effectiveness of about 10% (Tai, J. *Chromatogr. A* 1073(2005), 317), opens further possibilities for treating some neurological symptoms in patients suffering from mucopolysaccharidoses, which at present is entirely impossible.

SUMMARY OF THE INVENTION

The present invention is directed to the natural isoflavones and their semisynthetic derivatives which have been discovered to be useful in treatment of the diseases, at the base of which lies an excessive production or storage of glycosaminoglycans.

The present invention provides the use of the natural isoflavones and their semisynthetic derivatives or the pharmaceutically accepted salts thereof for the manufacture of a medicament for the therapeutic and/or prophylactic treatment of the diseases, at the base of which lies an excessive production or storage of glycosaminoglycans.

In one aspect the invention provides the use of the natural isoflavones and their semisynthetic derivatives or the pharmaceutically accepted salts thereof for the manufacture of a medicament for the therapeutic and/or prophylactic treatment of mucopolysaccharidose type I.

The other aspect of the invention is a pharmaceutical composition for the therapeutic and/or prophylactic treatment of the diseases, at the base of which lies an excessive production or storage of glycosaminoglycans, comprising the therapeutically effective amount of natural isoflavones or their semisynthetic derivatives or the pharmaceutically acceptable salts thereof as an active ingredient, together with the pharmaceutically acceptable vehicles and/or excipients.

The invention provides also the method for treating of the diseases, at the base of which lies an excessive production or storage of glycosaminoglycans, comprising administering the therapeutically effective amount of natural isoflavones or their semisynthetic derivative or the pharmaceutically acceptable salts thereof to the patient in the need of such a treatment.

DETAILED DESCRIPTION OF THE PREFERRED EMBODIMENT

Figure 1:
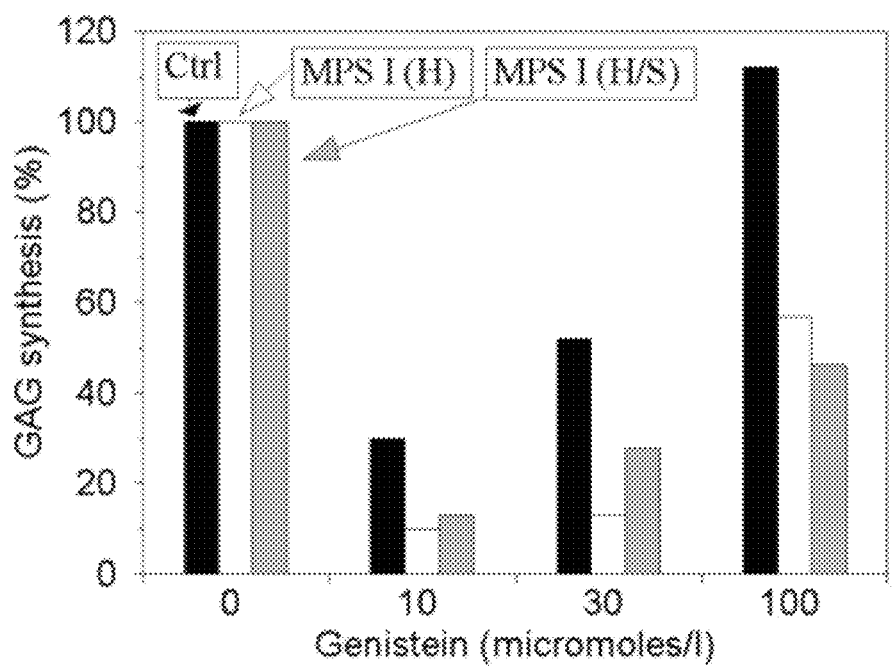
FIG. 1 shows glycosaminoglycans synthesis in fibroblasts of normal individuals (Ctrl) and of patients affected with MPS I, in vitro culture.

In view of their beneficial pharmacological properties, the natural isoflavones as genistein and their semisynthetic derivatives or the pharmaceutically accepted salts thereof may be used for the manufacture of a medicament for the therapeutic and/or prophylactic treatment of the diseases, at the base of which lies an excessive production or storage of glycosaminoglycans.

The compounds could be administered to the patient as the sole agents or as the components of a combined treatment, combining the compounds with the agents of confirmed therapeutic status in the treatment of mucopolysaccharidoses, for example with the enzymatic replacement therapy.

In the embodiment of the invention the preferred compounds are presented by formula (I)

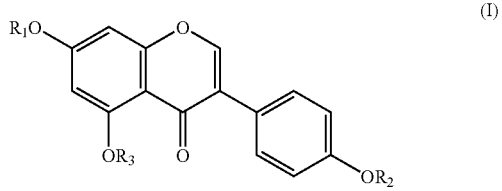

in which $R_1$ and $R_2$ are the same or different and are independently H or alkyl, alkenyl, aryl alkylaryl, alkylcarbonyl, arylcarbonyl or mono-, di- or oligosaccharide group, each of then optionally substituted by at least one acyl, alkyl, cycloalkyl, alkoxyalkyl, aryl, alkylaryl, carboxyl or cyano; and $R_3$ is H, acyl or alkyl.

The preferred derivative according to the invention is genistein, ie. the compound presented by formula (I) in which $R_1$, $R_2$ and $R_3$ are H.

The isoflavones and derivatives thereof may be administered to the patient as such or, preferably, in the form of a pharmaceutical composition, comprising the therapeutically effective amount of at least one isoflavone or its semisynthetic derivative represented by the formula (I) or the pharmaceutically acceptable salt thereof as an active ingredient, together with the pharmaceutically acceptable vehicles and/or excipients.

As therapeutically effective amount of isoflavone or its derivative represented by the formula (I) understood will be an amount, which is efficient in treatment and/or prevention of at least one type of mucopolysaccharidose, it means that it will be sufficient for limitation of GAG synthesis and/or for reducing the amount of the deposits accumulated in cells and at the same time ensuring the possibly low toxicity, tolerated by the patient. In the case of genistein, the beneficial therapeutic effect is observed within concentrations of about 10-20 micromoles/l.

Selection of the therapeutically effective dose of the active ingredient and dosage regimen of isoflavones and their derivatives depends on the type of disorder, age, weight and condition of the patient and they could be determined by a specialist on the ground of results of clinical trials and a general knowledge of the condition. By the use according to the invention, the daily dose of a derivative of isoflavone adjusted to the body mass of the patient, can amount from 1 to 50 mg/kg of a body mass depending on the way of administration, preferably about 5 mg/kg of a body mass. The daily dose of the active ingredient can be administered to the patient in the unit dosage form once per day or several times per day, optionally in a combination with other agents being therapeutically effective in the treatment of mucopolysaccharidoses. Such agents can be administered concurrently in the form of a combined formulation with a fixed dose or in separate formulations administered parallel or subsequently in the order and time intervals determined by a specialist.

The pharmaceutical composition, according to the invention, may be in any accepted in the pharmaceutical practice form, suitable for oral, parenteral, intranasal, sublingual, rectal, inhalatory or any other, administration. Especially the pharmaceutical composition may be in the form of tablet, pill, capsule, powder, granules, sterile solution or suspension, aerosol or suppository.

The proper methods of preparation of particular pharmaceutical forms according to the accepted practice, described for instance in the publication *Remington's Pharmaceutical Sciences,* Gennaro, ed. Mack Publishing Co., Easton, Pa. 1990, are known to the skilled in the art.

The solid forms, like tablets, pills, powders, granules or capsules, are prepared by accurate mixing the active ingredient with a pharmaceutical vehicle, such as corn starch, lactose, saccharose, sorbitol, talc, stearic acid, magnesium stearate, dicalcium phosphate or gum as well as other pharmaceutical diluents, for instance water, for formation of the solid premix, comprising the homogeneous mixture of compound according to the invention or to its pharmaceutically acceptable salt. The obtained in such a way premix can be used for tableting, making dragees or for filling capsules. Tablets or granules of the composition can be coated or prepared in other way to obtain a unit dosage form providing beneficially prolonged action. For production of such protecting or coating layers one can use several different substances, comprising different polymeric acids and their mixtures with such additives as shellac, cetyl alcohol or cellulose acetate.

The liquid forms of pharmaceutical compositions suitable for oral administration or for injection, according to the invention, comprise aqueous solutions, syrups, aqueous or oil suspended solids, emulsions with edible oils, such as cotton plant seed oil, sesame oil, coconut or peanut oil, as well as elixirs with similar pharmaceutical vehicles. Appropriate dispersing or suspending agents for aqueous suspended solids comprise synthetic and natural gums such as tragacanth, acacia, alginates, dextran, sodium carboxymethyl cellulose, methyl cellulose, polyvinyl pyrrolidone or gelatine.

The pharmaceutical composition in a solid form for oral administration may be in the form of tablet, capsule or granulate.

The solid oral formulation comprises at least one derivative of isoflavone dispersed within the vehicle together with other pharmaceutically acceptable excipients, such as binders, disintegrants and lubricants.

The proper vehicle (filler) will be selected by those skilled in the art, depending upon the required ready to use form of the medicine. Especially preferred diluent or filler of the solid pharmaceutical forms is lactose in different forms including the anhydrous, hydrated and spray-dried one. The most required form of lactose one can choose by considering the required solubility, homogeneity of substance comprised in the preparation, hardness, embrittlement and decomposition time of the tablet or capsule.

The binder, useful in the granulation stage, will be selected depending on the admissible viscosity and required hydration. Especially preferred binder is hydroxypropyl cellulose, especially the micromolecular one or microcrystalline cellulose.

The disintegrant, which applies to both granulates and loose powders, making easier the process of their decomposition, will be chosen from the group comprising different grades of starch, derivatives of cellulose, pectins, alginic acid and alginates, polivinylopirolidon. The preferred disintegrant is cross-linked polivinylopirolidon.

The proper lubricants, preventing sticking and crushing of tablets in the tabletting machine, are for instance calcium or magnesium stearate, paraffin, cetyl or stearyl alcohol. A preferred lubricant is magnesium stearate.

The solid pharmaceutical forms can be coated with a polymer selected from the group consisting of hydroxypropylmethyl cellulose, hydroxyethyl cellulose, hydroxymethylethyl cellulose, sodium salt of carboxymethyl cellulose, polivinylopirolidon, copolymers of methacrylic and acrylic acids esters, methyl and ethyl cellulose, as coating and subcoating layer, warranting its physical stability.

Appropriate coatings for using on the hydroxypropylmethyl cellulose layer constitute dry mixtures of components, which could be dispersed in water and used as aqueous dispersion for coating solid preparations with a film. For exemple, the coating consist of hydroxypropylmethyl cellulose, polyethylene glycol, polysorbate 80 and titanium dioxide. If necessary the solid preparation could be polished in a known manner, for instance with carnauba wax.

EXAMPLES

Example 1

Biological Tests

The isoflavones activity was evaluated by the measure of glycosaminoglycans synthesis in $^{35}$S-sulphate incorporation test comprising incubation of the radiolabelled $^{35}$S-sulfate into GAGs in cultured human skin fibroblasts derived from normal individuals (control) and patients affected with mucopolysaccharidose (Murata et al., Arch Biochem Biophys 2003; 413: 229-235). The level of glycosaminoglycans synthesis in the presence of genistein is significant decreasing in cultured human skin fibroblasts derived both from normal individuals and those affected with MPS 1 (FIG. 1).

Figure 2:
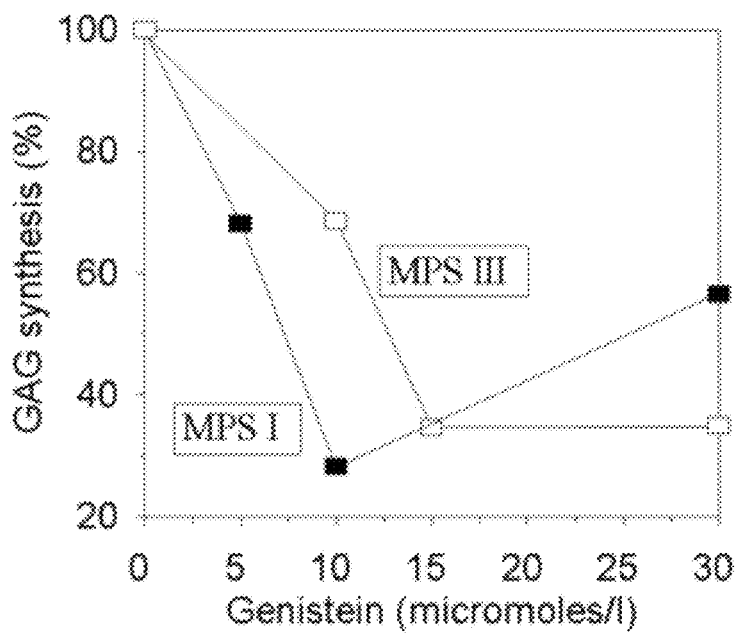
FIG. 2 shows GAG synthesis in fibroblasts derived from individuals with different MPS types in presence of genistein.

The tests have proved that glycosaminoglycans synthesis will be also significant reduced in the presence of genistein in cells derived from individuals with other types of MPS (FIG. 2).

The activity of inhibiting glycosaminoglycans synthesis demonstrates also a soya extract rich in isoflavones. As the tested compound there was used a commercial available soya extract enriched with isoflavones (Soyfem® from Biofarm, Poznań, Poland). The results of tests indicating the inhibition of GAG synthesis in the presence of Soyfem® in cultured fibroblasts are represented in FIG. 3.

Figure 4:
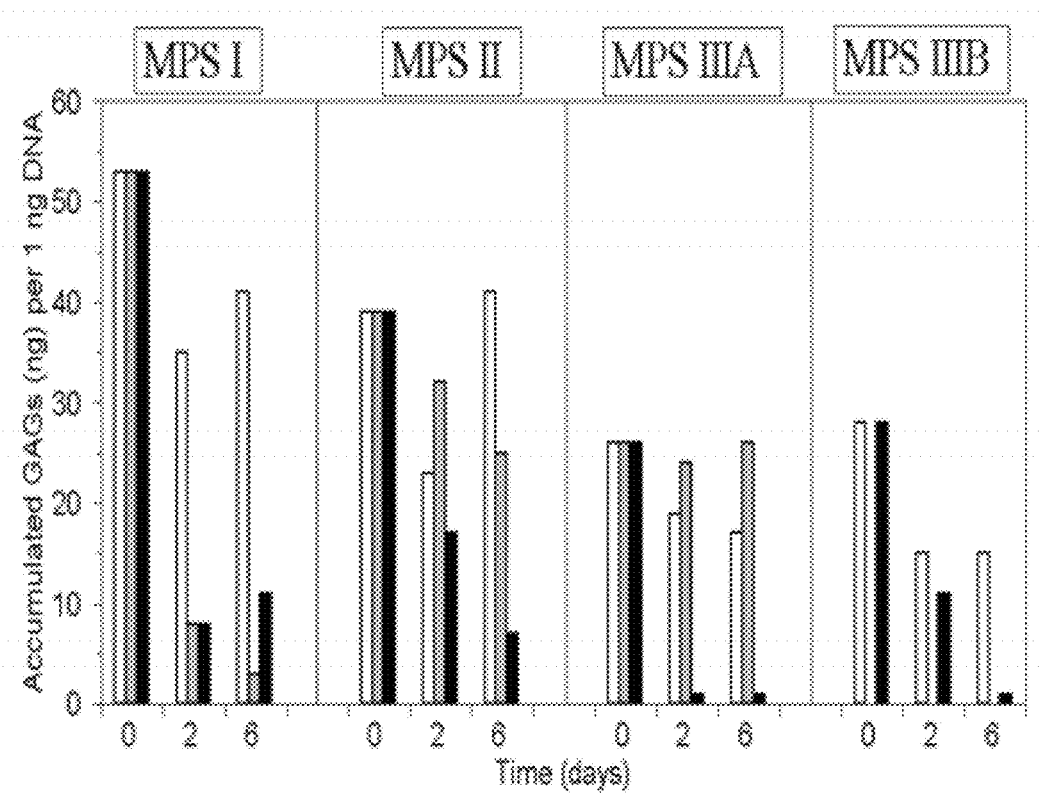
FIG. 4 shows activities of recombinant human α-L-iduronidase (100U/1000 ml; gray columns), genistein (10 micromoles/l; black columns) against GAG deposits, and empty columns represents control.

The results of next tests have proved that in the presence of genistein in the fibroblasts cells derived from patients affected with different MPSs not only takes place the inhibition of glycosaminoglycans accumulation but also their deposits are gradually removed (FIG. 4). After few days of cultivation under such conditions the effectiveness of removing GAG accumulated in cells derived from human individuals was comparable with the activity of recombinant human α-L-iduronidase (Aldurazyme) (FIG. 4). The electron microscope observation confirmed the phenomenon of decline of the before accumulated glycosaminoglycans from cells cultured in the presence of genistein and derivatives of isoflavones.

Figure 3:
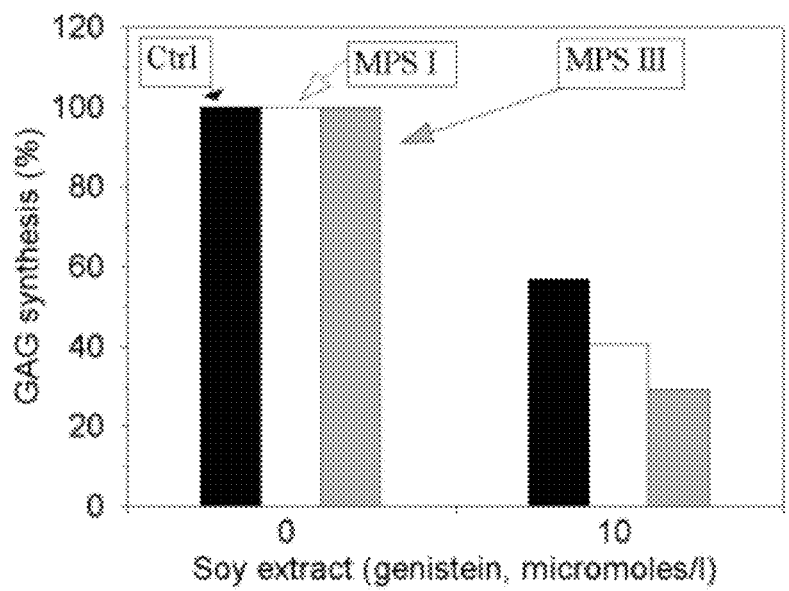
FIG. 3 shows GAG synthesis in fibroblasts in the presence of soya isoflavones extract (Soyfem®)

The activity of genistein and soya isoflavones against the GAG deposits in fibroblasts derived from human individuals affected with different types of MPS is presented in FIG. 3.

The decrease of GAG synthesis and reduction of the deposits accumulated in cells under genistein or soya isoflavones extract action has been observed at genistein concentrations of about 10-20 micromoles/l.

Further screening of semisynthetic derivatives of genistein represented by formula (I) has been performed comparing their activity to genistein as the reference (Table 2). The activity of derivatives of genistein represented by formula (I) in the glycosaminoglycans synthesis has been essayed in the radiolabelled $^{35}$S-sulphate incorporation test by using different human cell lines. The negative control was DMSO (diluent for genistein and all derivatives), the positive control—genistein. Genistein and the semisynthetic derivatives thereof were used in concentration of 30 μM. Experiment with each cell line has been repeated twice, and every measurement has been done twice.

TABLE 2

| | | Relative GAG synthesis (converted to 1 cell) | | |
| --- | --- | --- | --- | --- |
| Compound | Structure | Normal cells | MPS I | Inhibition in relation to genistein |
| Control | | 1 | 1 | –/– |
| Genistein | 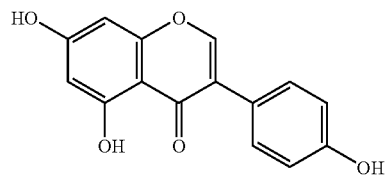 | 0.25 | 0.51 | 0 |

Glycosaminoglycans synthesis in the presence of semisynthetic genistein derivatives TABLE 2-continued Glycosaminoglycans synthesis in the presence of semisynthetic genistein derivatives

| Compound | Structure | Relative GAG synthesis (converted to 1 cell) | | Inhibition in relation to genistein |
|---|---|---|---|---|
| | | Normal cells | MPS I | |
| IFG-001 | 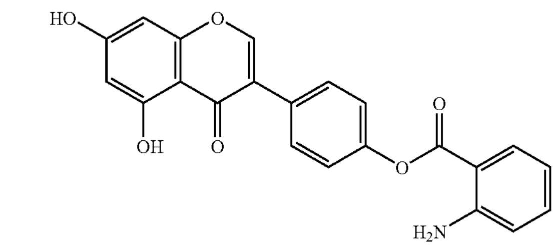 | 0.84 | 1.70 | –/– |
| IFG-018 | 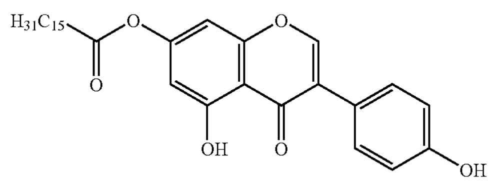 | 0.37 | 0.51 | 0/0 |
| IFG-021 | 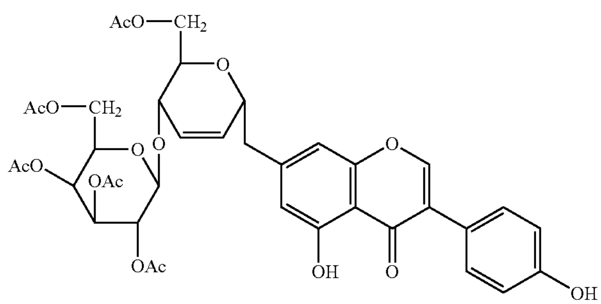 | 0.57 | 0.92 | –/– |
| IFG-027 | 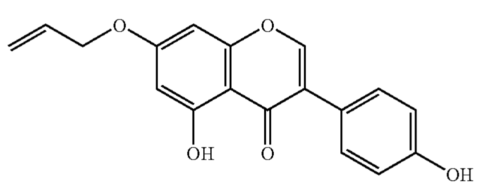 | 0.22 | 0.57 | 0/0 |
| IFG-032 | 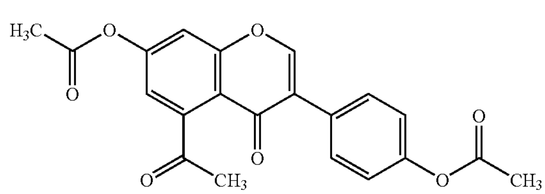 | 0.25 | 0.68 | 0/– |
| IFG-034 | 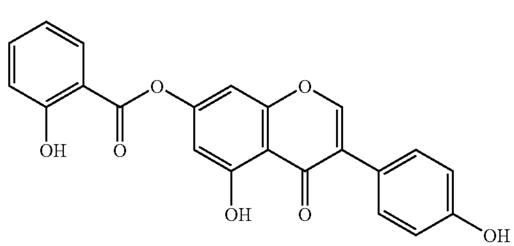 | 0.40 | 0.93 | –/– |

TABLE 2-continued

Glycosaminoglycans synthesis in the presence of semisynthetic genistein derivatives

| Compound | Structure | Relative GAG synthesis (converted to 1 cell) | | Inhibition in relation to genistein |
|---|---|---|---|---|
| | | Normal cells | MPS I | |
| IFG-035 | 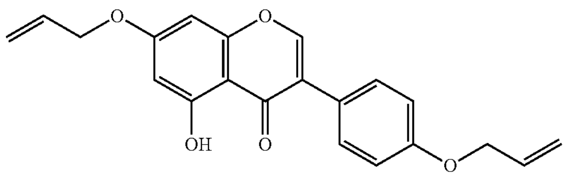 | 0.26 | 1.17 | 0/− |
| IFG-036 | 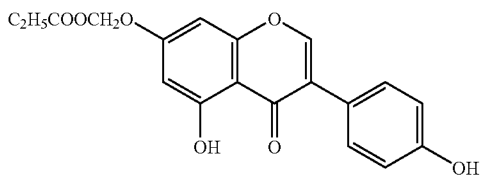 | 0.27 | 0.49 | 0/0 |
| IFG-037 | 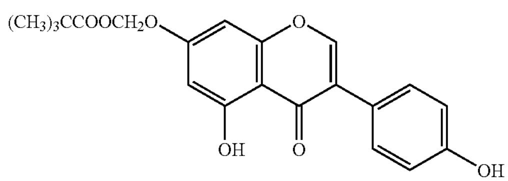 | 0.29 | 1.66 | 0/− |
| IFG-038 | 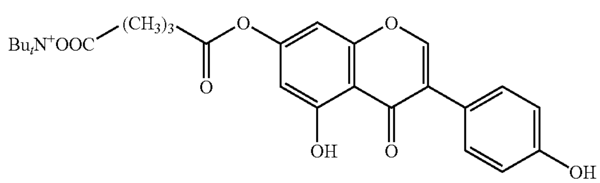 | 0.74 | 0.74 | −/− |
| IFG-042 | 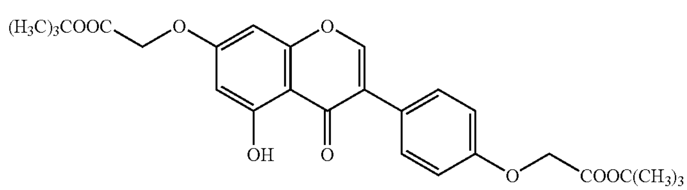 | 0.14 | 0.49 | +/0 |
| IFG-043 | 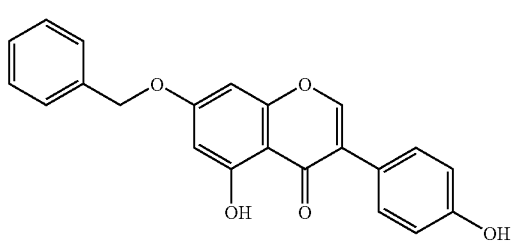 | 0.17 | 0.44 | +/0 |
| IFG-046 | 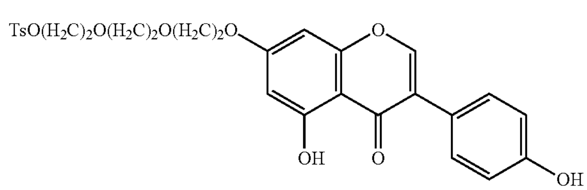 | 1.80 | 0.49 | −/0 |

TABLE 2-continued

Glycosaminoglycans synthesis in the presence of
semisynthetic genistein derivatives

| | | Relative GAG synthesis (converted to 1 cell) | | |
|---|---|---|---|---|
| Compound | Structure | Normal cells | MPS I | Inhibition in relation to genistein |
| IFG-048 | | 0.70 | 0.92 | –/– |
| IFG-050 | | 0.10 | 0.73 | –/– |
| IFG-051 | | 0.32 | 0.96 | 0/– |
| IFG-052 | | 0.75 | 0.85 | –/– |
| IFG-053 | | 0.30 | 0.52 | 0/0 |

TABLE 2-continued

Glycosaminoglycans synthesis in the presence of semisynthetic genistein derivatives

| Compound | Structure | Relative GAG synthesis (converted to 1 cell) | | Inhibition in relation to genistein |
|---|---|---|---|---|
| | | Normal cells | MPS I | |
| IFG-054 | 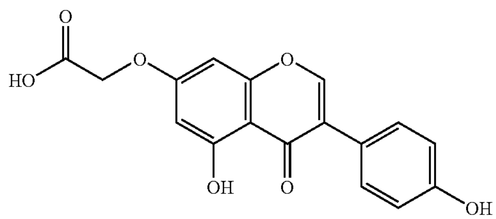 | 0.30 | 0.53 | 0/0 |
| IFG-060 | 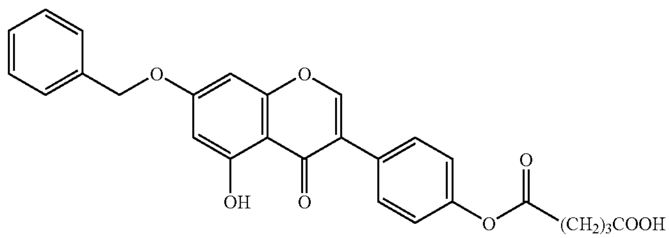 | 0.43 | 0.31 | −/+ |
| IFG-061 | 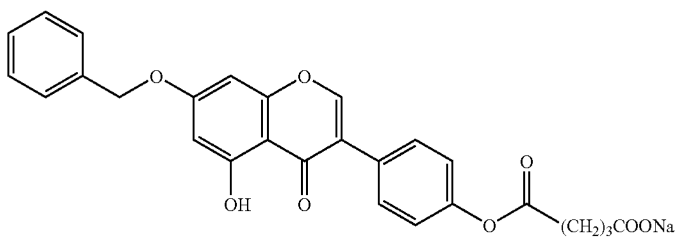 | 0.28 | 0.46 | 0/0 |
| IFG-062 | 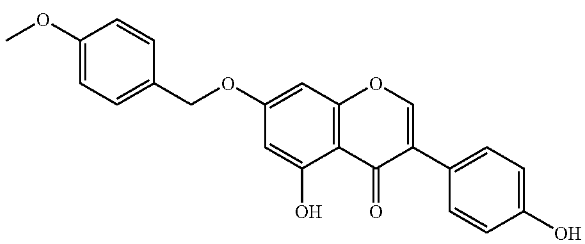 | 3.16 | 5.61 | —/— |
| IFG-063 | 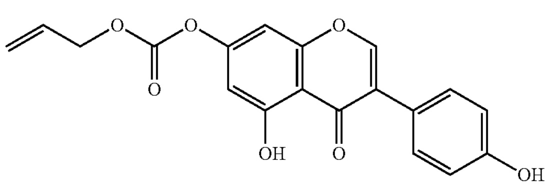 | 0.75 | 1.87 | −/− |
| IFG-064 | 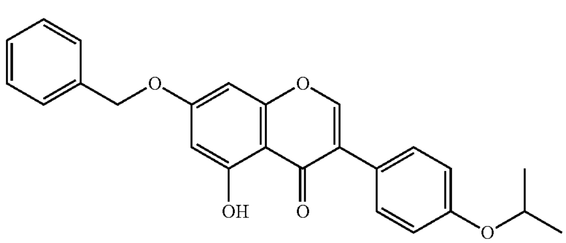 | 0.68 | 0.60 | −/− |

TABLE 2-continued

Glycosaminoglycans synthesis in the presence of semisynthetic genistein derivatives

| Compound | Structure | Relative GAG synthesis (converted to 1 cell) | | Inhibition in relation to genistein |
|---|---|---|---|---|
| | | Normal cells | MPS I | |
| IFG-065 | 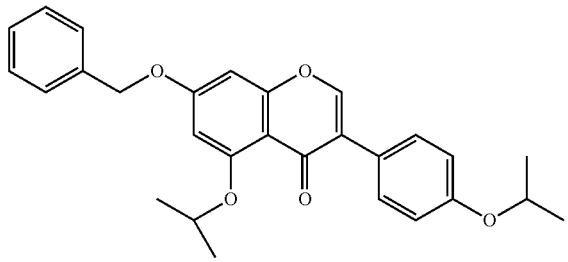 | 1.52 | 0.97 | –/– |
| IFG-066 | 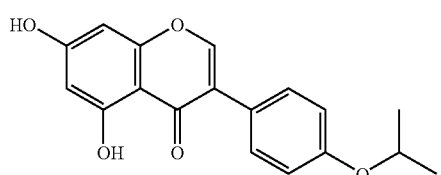 | 0.23 | 0.44 | 0/0 |
| IFG-067 | 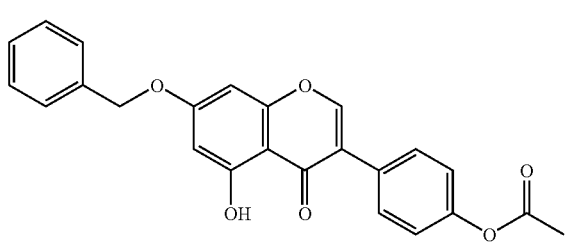 | 0.67 | 0.61 | –/– |

"–" inhibition weaker than by genistein;
"0" inhibition comparable to genistein;
"+" inhibition stronger than by genistein.

The compounds IFG-18, IFG-42 and IFG-50 demonstrated in the above test stronger influence on GAG synthesis than genistein, and the compounds IFG-27, IFG-36, IFG-38, IFG-43 and IFG-53—an activity comparable with genistein. The compounds IFG-32, IFG-35, IFG-48, IFG-51, IFG-52 and IFG-64 proved the activity comparable with genistein, but only for one cell line. The results of the above experiments confirmed the potential usefulness of derivatives of isoflavone presented by formula (I) in the treatment and/or prevention of mucopolysaccharidoses.

Example 2

| Tablet formulation: | |
|---|---|
| Genistein | 50 mg |
| Corn starch | 16 mg |
| Colloidal silicon dioxide | 1 mg |
| Magnesium stearate | 1 mg |
| K-30 povidone | 3 mg |
| Pregelatinized starch | 4 mg |
| Microcrystalline cellulose | 25 mg |
| Lactose | 200 mg |

| Capsule formulation: | |
|---|---|
| Genistein | 10 mg |
| Corn starch | 2 mg |
| Colloidal silicon dioxide | 0.2 mg |
| Magnesium stearate | 0.4 mg |
| Lactose | 20 mg |

What is claimed is:

1. A pharmaceutical composition comprising a pharmaceutically acceptable excipient; and a compound of formula (I), or a pharmaceutically acceptable salt thereof,

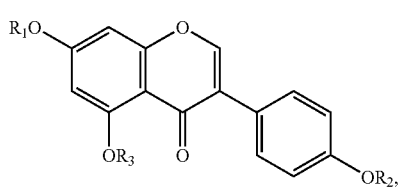

(I)

wherein
$R_1$ is $-C(O)C_{15}H_{31}$, $R_2$ is H, and $R_3$ is H; and
said compound of formula (I), or said pharmaceutically acceptable salt thereof is useful in the treatment of mucopolysaccharidosis and is provided in a therapeutically effective amount for the treatment of mucopolysaccharidosis.

2. A pharmaceutical composition comprising a pharmaceutically acceptable excipient; and a compound of formula (I), or a pharmaceutically acceptable salt thereof,

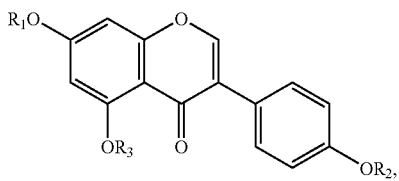

(I)

wherein $R_1$ is $(CH_3)_3COOCCH_2$—, $R_2$ is $(CH_3)_3COOCCH_2$—, and $R_3$ is H; and said compound of formula (I), or said pharmaceutically acceptable salt thereof is useful in the treatment of mucopolysaccharidosis and is provided in a therapeutically effective amount for the treatment of mucopolysaccharidosis.

3. A pharmaceutical composition comprising a pharmaceutically acceptable excipient; and a compound of formula (I), or a pharmaceutically acceptable salt thereof,

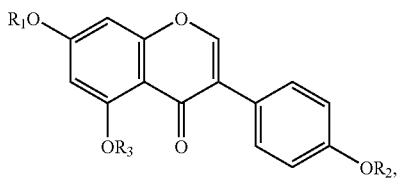

(I)

wherein $R_1$ is oxiranylmethyl, $R_2$ is H, and $R_3$ is H; and said compound of formula (I), or said pharmaceutically acceptable salt thereof is useful in the treatment of mucopolysaccharidosis and is provided in a therapeutically effective amount for the treatment of mucopolysaccharidosis.

4. A method of treatment of mucopolysaccharidosis, the method comprising administering to a patient in the need of such treatment a compound of formula (I) or a pharmaceutically acceptable salt thereof,

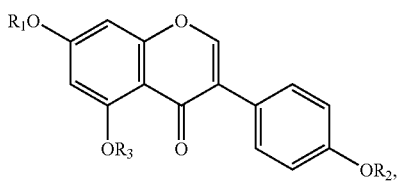

(I)

wherein $R_1$ is —C(O)C$_{15}$H$_{31}$, $R_2$ is H, and $R_3$ is H.

5. A method of treatment of mucopolysaccharidosis, the method comprising administering to a patient in the need of such treatment a compound of formula (I) or a pharmaceutically acceptable salt thereof,

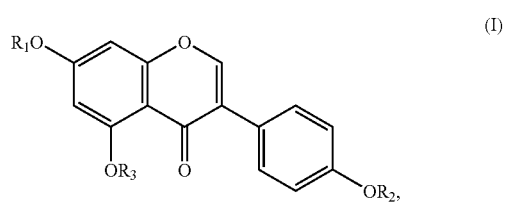

(I)

wherein $R_1$ is $(CH_3)_3COOCCH_2$—, $R_2$ is $(CH_3)_3COOCCH_2$—, and $R_3$ is H.

6. A method of treatment of mucopolysaccharidosis, the method comprising administering to a patient in the need of such treatment a compound of formula (I) or a pharmaceutically acceptable salt thereof,

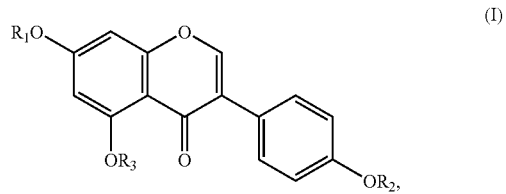

(I)

wherein $R_1$ is oxiranylmethyl, $R_2$ is H, and $R_3$ is H.

7. A method of treatment of mucopolysaccharidosis, comprising administering to a patient in the need of such treatment a therapeutically effective amount of a compound of formula (I), or a pharmaceutically acceptable salt thereof,

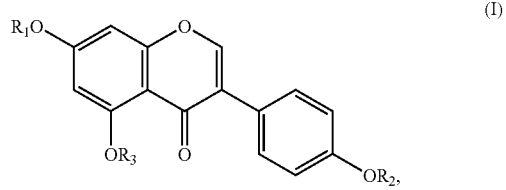

(I)

wherein $R_1$, $R_2$ and $R_3$ are each H.

8. A method of treatment of mucopolysaccharidosis, comprising administering to a patient in the need of such treatment a therapeutically effective amount of a compound of formula (I), or a pharmaceutically acceptable salt thereof,

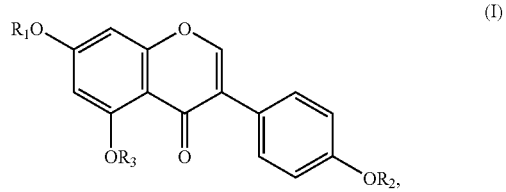

(I)

wherein $R_1$ is —C(O)C$_{15}$H$_{31}$, $R_2$ is H, and $R_3$ is H.

9. A method of treatment of mucopolysaccharidosis, comprising administering to a patient in the need of such treatment a therapeutically effective amount of a compound of formula (I), or a pharmaceutically acceptable salt thereof,

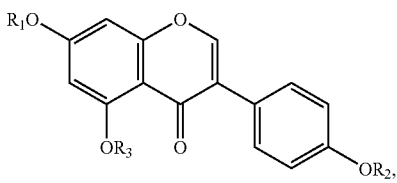

(I)

wherein $R_1$ is $(CH_3)_3COOCCH_2$—, $R_2$ is $(CH_3)_3COOCCH_2$—, and $R_3$ is H.

10. A method of treatment of mucopolysaccharidosis, comprising administering to a patient in the need of such treatment a therapeutically effective amount of a compound of formula (I), or a pharmaceutically acceptable salt thereof,

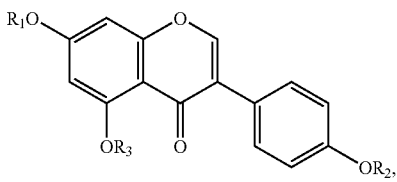

(I)

wherein $R_1$ is oxiranylmethyl, $R_2$ is H, and $R_3$ is H.

11. A method of treatment of mucopolysaccharidosis, the method comprising administering to a patient in the need of such treatment a therapeutically effective amount of a compound selected from: 4'-(2-aminobenzoyloxy)-5,7-dihydroxy-3-phenylchromen-4-one; 4',5-dihydroxy-7-hexadecanoyloxy-3-phenylchromen-4-one; 2-(acetoxymethyl)-6-(2-(acetoxymethyl)-6-((5-hydroxy-3-(4-hydroxyphenyl)-4-oxo-4H-chromen-7-yl)methyl)-3,6-dihydro-2H-pyran-3-yloxy)tetrahydro-2H-pyran-3,4,5-triyl triacetate; 4',5-dihydroxy-7-allyloxy-3-phenylchromen-4-one; 4',5-dihydroxy-7-(2-hydroxybenzoyloxy)-3-phenylchromen-4-one; 4',7-diallyloxy-5-hydroxy-3-phenylchromen-4-one; 4',5-dihydroxy-7-propionyloxymethoxy-3-phenylchromen-4-one; 4',5-dihydroxy-7-(tert-butoxycarbonylmethoxy)-3-phenylchromen-4-one; 4',5-dihydroxy-7-(4-carboxybutyryloxy)-3-phenylchromen-4-one; 4',7-di(tert-butoxycarbonylmethoxy)-5-hydroxy-3-phenylchromen-4-one; 4',5-dihydroxy-7-benzyloxy-3-phenylchromen-4-one; 2-(2-(2-(5-hydroxy-3-(4-hydroxyphenyl)-4-oxo-4H-chromen-7-yloxy)ethoxy)ethoxy)ethyl 4-methylbenzenesulfonate; 4'-(tert-butoxycarbonylmethoxy)-5,7-dihydroxy-3-phenylchromen-4-one; 4',5-dihydroxy-7-oxiranylmethoxy-3-phenylchromen-4-one; 3-(4-(allyloxy)phenyl)-7-(benzyloxy)-5-hydroxy-4H-chromen-4-one; 4-(7-(allyloxy)-5-hydroxy-4-oxo-4H-chromen-3-yl)phenyl 2-acetoxybenzoate; 4'-(3,5-bis(1-cyano-1-methylethyl)benzyloxy)-5-hydroxy-7-benzyloxy-3-phenylchromen-4-one; 4',5-dihydroxy-7-carboxymethoxy-3-phenylchromen-4-one; 2-(5-hydroxy-3-(4-hydroxyphenyl)-4-oxo-4H-chromen-7-yloxy)acetic acid; 4'-(4-carboxybutyryloxy)-5-hydroxy-7-benzyloxy-3-phenylchromen-4-one; 4',5-dihydroxy-7-(4-methoxybenzyloxy)-3-phenylchromen-4-one; allyl 5-hydroxy-3-(4-hydroxyphenyl)-4-oxo-4H-chromen-7-yl carbonate; 7-(benzyloxy)-5-hydroxy-3-(4-isopropoxyphenyl)-4H-chromen-4-one; 7-(benzyloxy)-5-isopropoxy-3-(4-isopropoxyphenyl)-4H-chromen-4-one; 5,7-dihydroxy-3-(4-isopropoxyphenyl)chromen-4-one; 4'-acetoxy-5-hydroxy-7-benzyloxy-3-phenylchromen-4-one; or a pharmaceutically acceptable salt thereof.

* * * * *